United States Patent
Lai et al.

(10) Patent No.: US 11,166,916 B2
(45) Date of Patent: Nov. 9, 2021

(54) CARBON QUANTUM DOTS AND PREPARATION PROCESS AND USE THEREOF

(71) Applicant: CHANG GUNG UNIVERSITY, Taoyuan (TW)

(72) Inventors: Jui-Yang Lai, Taoyuan (TW); Chih-Ching Huang, Taoyuan (TW); Hong-Jyuan Jian, Taoyuan (TW)

(73) Assignee: Chang Gung University, Taoyuan (TW)

( * ) Notice: Subject to any disclaimer, the term of this patent is extended or adjusted under 35 U.S.C. 154(b) by 64 days.

(21) Appl. No.: 16/888,585

(22) Filed: May 29, 2020

(65) Prior Publication Data
US 2021/0177763 A1 Jun. 17, 2021

(30) Foreign Application Priority Data

Dec. 12, 2019 (TW) .................. 108145453

(51) Int. Cl.
| | | |
|---|---|---|
| *A61P 31/04* | (2006.01) | |
| *A01N 33/04* | (2006.01) | |
| *A01N 25/12* | (2006.01) | |
| *C01B 32/15* | (2017.01) | |
| *B82Y 40/00* | (2011.01) | |
| *B82Y 5/00* | (2011.01) | |
| *A61K 31/137* | (2006.01) | |
| *A61K 31/132* | (2006.01) | |
| *A61K 9/19* | (2006.01) | |
| *A61K 31/131* | (2006.01) | |

(52) U.S. Cl.
CPC .............. *A61K 9/19* (2013.01); *A01N 25/12* (2013.01); *A01N 33/04* (2013.01); *A61K 31/131* (2013.01); *A61K 31/132* (2013.01); *A61K 31/137* (2013.01); *A61P 31/04* (2018.01); *C01B 32/15* (2017.08); *B82Y 5/00* (2013.01); *B82Y 40/00* (2013.01); *C01P 2004/64* (2013.01)

(58) Field of Classification Search
None
See application file for complete search history.

(56) References Cited

PUBLICATIONS

Harroun et al. ACS Infectious Disease 2017 3:777-779 (Year: 2017).*
Jian et al. ACS Nano 2017 11:6703-6716 (Year: 2017).*
Xiao et al. Nanomaterials 2018 8:854, 1-13 (Year: 2018).*
Lan et al. Journal of Materials Chemistry B 2017 5:5265-5271 (Year: 2017).*

* cited by examiner

*Primary Examiner* — Robert A Wax
*Assistant Examiner* — Caralynne E Helm
(74) *Attorney, Agent, or Firm* — Hammer & Associates, P.C.

(57) ABSTRACT

Disclosed herein is a carbon quantum dot produced by the step of subjecting dopamine and spermine to a pyrolysis treatment at 250° C. Also disclosed herein is use of the carbon quantum dot for treating a bacterial infection, and for inhibiting bacterial growth and biofilm formation.

9 Claims, 14 Drawing Sheets

CARBON QUANTUM DOTS AND PREPARATION PROCESS AND USE THEREOF

CROSS-REFERENCE TO RELATED APPLICATION

This application claims priority of Taiwanese Patent Application No. 108145453, filed on Dec. 12, 2019.

FIELD

The present disclosure relates to a carbon quantum dot and a method of preparing the same. The present disclosure also relates to use of this carbon quantum dot to treat a bacterial infection and to inhibit bacterial growth and biofilm formation.

BACKGROUND

Bacterial pathogens, or disease-producing microorganisms, can infect a host by one of several mechanisms and cause significant morbidity and mortality. They may enter through a break in the skin, they may be introduced by vector transmission, or they may interact with a mucosal surface. Disease ensues following infection of the host, when the potential of the pathogen to disrupt normal bodily functions is fully expressed. Common bacterial pathogens include *Staphylococcus aureus* (such as methicillin-resistant *Staphylococcus aureus* (MRSA)), *Escherichia coli*, *Pseudomonas aeruginosa*, and *Salmonella enteritidis*.

Biofilms are medically and industrially important because they can accumulate on a wide variety of substrates and are resistant to antimicrobial agents and detergents. Microbial biofilms develop when microorganisms adhere to a surface and produce extracellular polymers that facilitate adhesion and provide a structural matrix. Therefore, inhibiting adhesion to surfaces is important. These surfaces may be inert, non-living materials or living tissues. Recently, medical devices or materials (such as urinary catheters, vascular grafts, and contact lenses) have been widely used. However, improper cleaning and storage of such devices or materials may cause biofilm formation, which can lead to bacterial infections (such as endocarditis, osteomyelitis, sinusitis, urethral infections, chronic prostatitis, and keratitis).

Carbon quantum dots (CQDs), which serve as a new type of carbon material, not only has good stability and biocompatibility, but also has abundant surface functional groups and a special structure of graphene carbon group. CQDs have been widely used in light chemicals, biological imaging, biomedical engineering, and other fields because of the superior photoluminescence properties.

It has been reported that CQDs prepared from biogenic polyamines (PAs) (such as putrescine, spermidine, and spermine) have been used as an antibacterial agent for topical treatment of bacterial infection. For instance, Jian H. J. et al. disclose a one-step method to synthesize carbon quantum dots from biogenic polyamines. Briefly, CQDs from polyamines (CQDPAs) were prepared by directly pyrolyzing putrescine, spermidine, or spermine at 210° C., 240° C., 270° C., or 300° C. for 3 hours in the solid state. The thus obtained CQDPAs were then dispersed in deionized (DI) water and sonicated for 30 minutes. Larger particles were removed by centrifugation with a relative centrifugal force (RCF) of 20000 g for 60 minutes. The CQDPAs in the supernatant were collected and purified through dialysis. The experimental results reveal that the yields of the CQD-PAs product obtained from spermine (CQDSpms) or putrescine (CQDPuts) are relatively low compared to those of CQDs from spermidine (CQDSpds) synthesized at 210-270° C. Furthermore, relative to free spermidine, CQDSpds exhibit much higher antibacterial activity not only against non-multidrug-resistant bacteria but also against multidrug-resistant bacteria (MRSA) due to their strong disintegration effect on the bacterial membrane. Topical ocular administration of CQDSpds can induce the opening of the tight junction of corneal epithelial cells, thereby leading to great antibacterial treatment of *Staphylococcus aureus*-induced bacterial keratitis in rabbits. The experimental results indicate that CQDSpds are a promising antibacterial candidate for clinical applications in treating eye-related bacterial infections and even persistent bacteria induced infections. (Jian H. J. et al. (2017), *ACS Nano*, 11:6703-6716).

In spite of the aforesaid, there is still a need to develop a new carbon quantum dot that can more satisfactorily inhibit bacterial growth and biofilm formation.

SUMMARY

Accordingly, in a first aspect, the present disclosure provides a carbon quantum dot produced by the step of:

subjecting dopamine and spermine to a pyrolysis treatment at 250° C.

In a second aspect, the present disclosure provides a composition including a carbon quantum dot as described above.

In a third aspect, the present disclosure provides a method for treating a bacterial infection, which includes administering to a subject in need thereof a carbon quantum dot as described above.

In a fourth aspect, the present disclosure provides a method for inhibiting bacterial growth and biofilm formation, which includes applying a carbon quantum dot as described above onto an object.

In a fifth aspect, the present disclosure provides a process for producing a carbon quantum dot, which includes the step of:

subjecting dopamine and spermine to a pyrolysis treatment at 250° C.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which.

DETAILED DESCRIPTION

Figure 1:
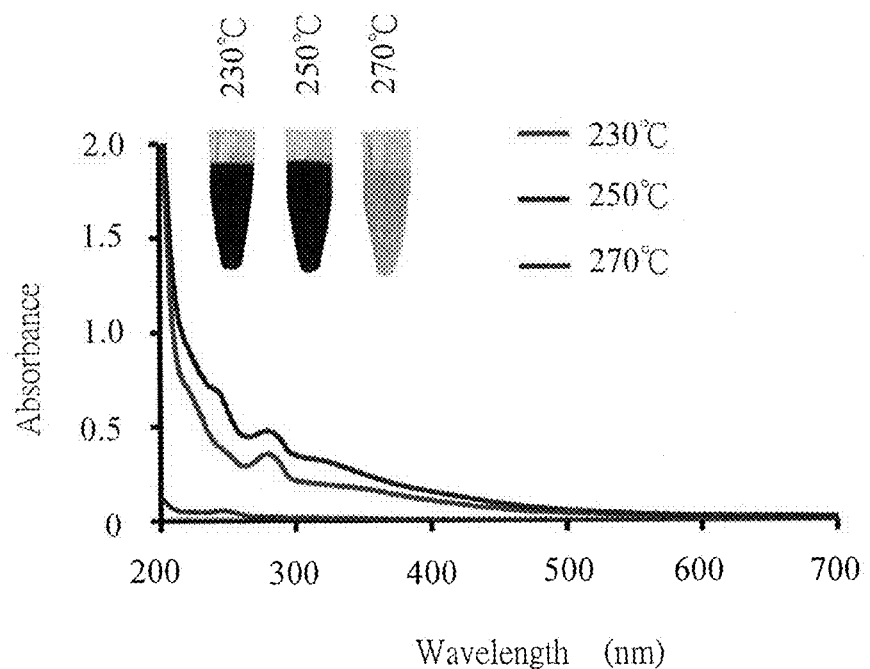
FIG. 1 shows the UV-visible absorption spectra of dialysates prepared at different pyrolysis temperatures.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a carbon quantum dot produced by the step of:

subjecting dopamine and spermine to a pyrolysis treatment at 250° C.

According to the present disclosure, a ratio of dopamine to spermine ranges from 1:0.25 (w/w) to 1:4 (w/w). In an exemplary embodiment, the ratio of dopamine to spermine is 1:0.42 (w/w). In another exemplary embodiment, the ratio of dopamine to spermine is 1:2.33 (w/w). In yet another exemplary embodiment, the ratio of dopamine to spermine is 1:1 (w/w).

According to the present disclosure, the carbon quantum dot may have a particle size ranging from 3 to 10 nm. In an exemplary embodiment, the carbon quantum dot has a particle size of 4 nm.

According to the present disclosure, the carbon quantum dot may have a zeta potential ranging from +5 to +50 mV. In an exemplary embodiment, the carbon quantum dot has a zeta potential of +33 mV.

According to the present disclosure, the carbon quantum dot may have a covalent bond selected from the group consisting of C—C, C—O, C—N, C=C, C=O, C=N, and combinations thereof.

It should be appreciated that the operating conditions of the pyrolysis treatment may vary, depending on the peripheral instruments and equipment used, the proportion of the amounts of dopamine and spermine used, etc. The actual operating conditions necessary for the pyrolysis treatment are well known in the art, and can be determined without undue experimentation.

According to the present disclosure, the pyrolysis treatment may be conducted at 250° C. for 2 to 4 hours. In an exemplary embodiment, the pyrolysis treatment is conducted at 250° C. for 2 hours.

The present disclosure also provides a method for treating a bacterial infection, which includes administering to a subject in need thereof a carbon quantum dot as described above.

As used herein, the term "treat" or "treatment" means lessening, inducing stasis of, or postponing or reducing the progression, development, onset, or severity of the disease or condition or severity of one or more symptoms associated with a disease or disorder or condition described herein, or ameliorating existing uncontrolled or unwanted symptoms, preventing additional symptoms, or relieving or alleviating the intensity and/or duration of a manifestation of a disorder experienced by a subject. The term "treat" also includes prophylactically preventing, curing, healing, altering, remedying, ameliorating, improving, or affecting a condition (e.g., a disease), the symptoms of the condition, or the predisposition toward the condition.

As used herein, the term "bacterial infection" refers to the undesired proliferation or presence of invasion of pathogenic microbes in a host organism. This includes the excessive growth of microbes that are normally present in or on the body of a mammal or other organism. More generally, a bacterial infection can be any situation in which the presence of a bacterial population(s) is damaging to a host mammal. Thus, a bacterial infection exists when excessive numbers of a bacterial population are present in or on a mammal's body, or when the effects of the presence of a bacterial population(s) are damaging the cells or other tissue of a mammal.

According to the present disclosure, the bacterial infection may be selected from the group consisting of keratitis, conjunctivitis, endocarditis, osteomyelitis, sinusitis, urinary tract infection, chronic prostatitis, meningitis, and combinations thereof. In an exemplary embodiment, the bacterial infection is keratitis.

According to the present disclosure, the carbon quantum dot may be prepared in the form of a pharmaceutical composition. The pharmaceutical composition may be formulated into a suitable dosage form for parenteral or topical administration using technology well known to those skilled in the art.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration. In certain embodiments, the pharmaceutical composition is formulated into a suitable dosage form for intravenous injection. In other embodiments, the pharmaceutical composition is formulated into a suitable dosage form for subcutaneous injection.

The pharmaceutical composition according to the present disclosure may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

The dosage and frequency of administration of the pharmaceutical composition according to the present disclosure may vary depending on the following factors: the severity of the disease to be alleviated, the route of administration, and the age, physical condition and response of the subject to be treated.

The present disclosure also provides a method for inhibiting bacterial growth and biofilm formation, which includes applying a carbon quantum dot as described above onto an object.

As used herein, the term "biofilm formation" refers to the attachment of microorganisms to surfaces and the subsequent development of multiple layers of cells.

As used herein, the term "inhibition" or "inhibiting" refers to a decrease of biofilm associated microorganism formation and/or growth. The microorganisms may include gram-positive or gram-negative bacteria, yeasts, and fungi.

According to the present disclosure, the object may be a medical device, a medical instrument, a dressing, a bandage, a food preparation surface, a food packaging surface, a manufacturing surface, a consumer good, a water treatment system, a water delivery system, or a ventilation system.

In certain embodiments, the object may be selected from the group consisting of a denture, a mouth guard, a dairy line, a water line, an adhesive bandage, a component of an HVAC system, a component of a water treatment facility, a component of a vacuum or a vacuum cleaner, a vacuum cleaner bag, a vacuum cleaner filter, an air filter, a component of a cooling tower, a toy, a window, a door, a window frame, a doorframe, a medical instrument, a dental instrument, a bathroom tile, a kitchen tile, food industry processing instruments, hospital tables and beds, an animal water dish, a washing machine, a dishwasher, a towel, a dish, a bowl, a utensil, a cup, a glass, a cutting board, a dish drying tray, a whirlpool bathtub, a sink, a toilet, a toilet seat, a swimming pool, a birdbath, a planter, a garden hose, a fish pond, an oil pipe, a gas pipe, a dairy line filter, a line used in food and beverage manufacturing, a cosmetic container, an outdoor pond liner, a tap and water spout, a humidifier, a humidifier filter, a bathroom tile, a bathroom fixture, a toilet lid, a swimming pool liner, a swimming pool skimmer, a swimming pool filter, a hot tub line, a hot tub filter, a washing machine liner, a dishwasher liner, an animal water dish, a food storage container, a beverage storage container, a plate, a cup, a fork, a knife, a spoon, a garbage bag, and a counter top.

According to the present disclosure, biofilm formation may be caused by a microbe selected from the group consisting of *Staphylococcus aureus* (such as mexillin-resistant *Staphylococcus aureus* (MRSA)), *Escherichia coli*, *Pseudomonas aeruginosa, Salmonella enteritidis*, and combinations thereof.

The disclosure will be further described by way of the following examples. However, it should be understood that the following examples are solely intended for the purpose of illustration and should not be construed as limiting the disclosure in practice.

EXAMPLES

General Experimental Materials:
1. The bacterial pathogens used in the following experiments are listed in Table 1.

TABLE 1

| Bacteria | Strain | Source |
| --- | --- | --- |
| *Escherichia coli* | BCRC 10316 | Bioresources Collection and Research Center (BCRC) of Food Industry Research and Development Institute (FIRDI) (Hsinchu City, Taiwan) |
| *Staphylococcus aureus* | ATCC 9144 | American Type Culture Collection (ATCC, Manassas, Va., USA) |
| *Pseudomonas aeruginosa* | ATCC 10145 | |
| *Salmonella enteritidis* | ATCC 13076 | |
| Methicillin-resistant *Staphylococcus aureus* (MRSA) | ATCC 33592 | |

2. LB broth and agar used in the examples were purchased from BioShop Canada Inc.
3. Mannitol, NaCl, peptone, beef extract, dopamine(DA), spermine (SPM), spermidine (SPD), and putrescine (PUT) used in the examples were all purchased from Sigma-Aldrich.

General Procedures:
1. Statistical Analysis

The experimental data are expressed as mean±standard error of the mean (SEM), and were analyzed via Student's t-test so as to assess the difference between all the groups. Statistical significance is indicated by $p<0.05$.

Example 1. Preparation of Carbon Quantum Dot of Present Disclosure

A. Pyrolysis of dopamine at different temperatures 0.04 g of dopamine was evenly mixed with 0.5 mL of deionized water, and the resultant mixture was heated at a designated temperature (230° C., 250° C., or 270° C.) for 2 hours. The solid residue thus obtained was allowed to cool to room temperature, followed by adding 5 mL of deionized water. Subsequently, centrifugation at 20,000 g was performed for 60 minutes, and the resultant supernatant was collected, followed by conducting dialysis using a dialysis membrane with a molecular weight cut-off value of 1 kDa and deionized water for 10 hours, so as to obtain a dialysate. The dialysate was diluted 10-fold by deionized water, followed by obtaining a UV-visible absorption spectrum and a fluorescence spectrum using a monochromatic microplate spectrophotometer (Synergy 4 Multi-Mode, Biotek Instruments, Winooski, Vt., USA).

Figure 2:
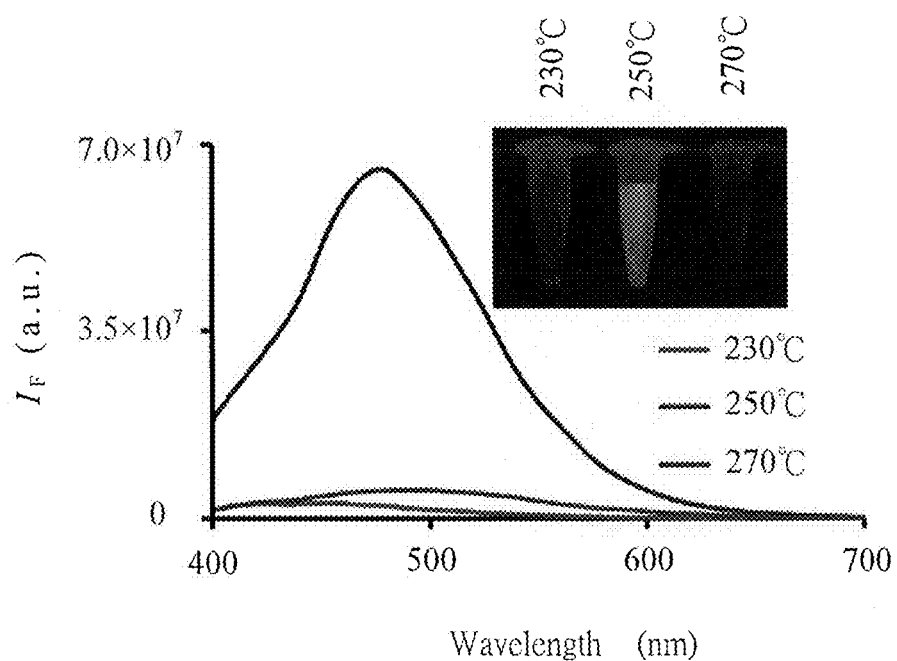
FIG. 2 shows the fluorescence spectra of the dialysates prepared at different pyrolysis temperatures.
Figure 3:
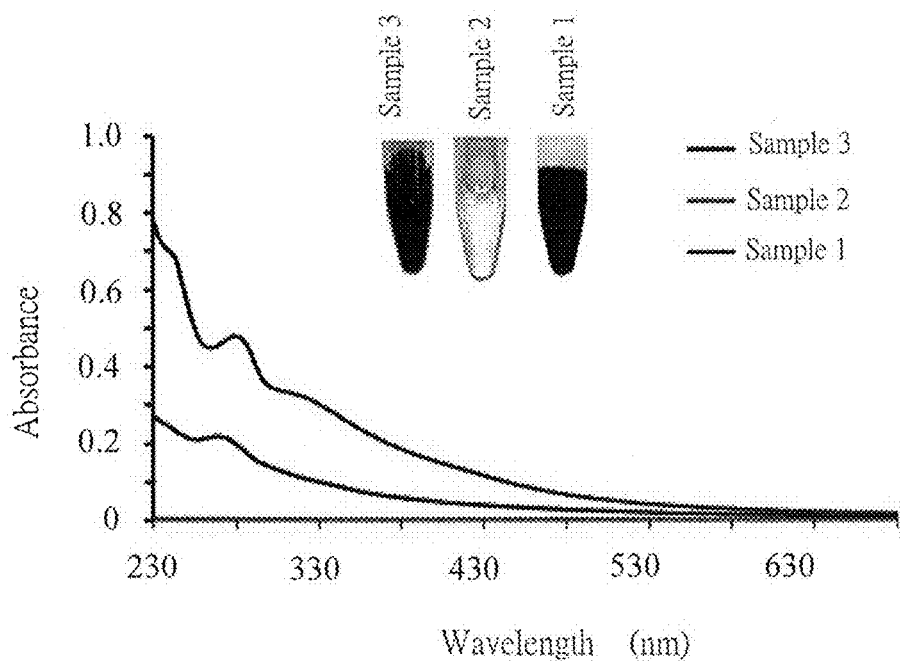
FIG. 3 shows the UV-visible absorption spectra of samples 1-3 of Example 1, infra.
Figure 4:
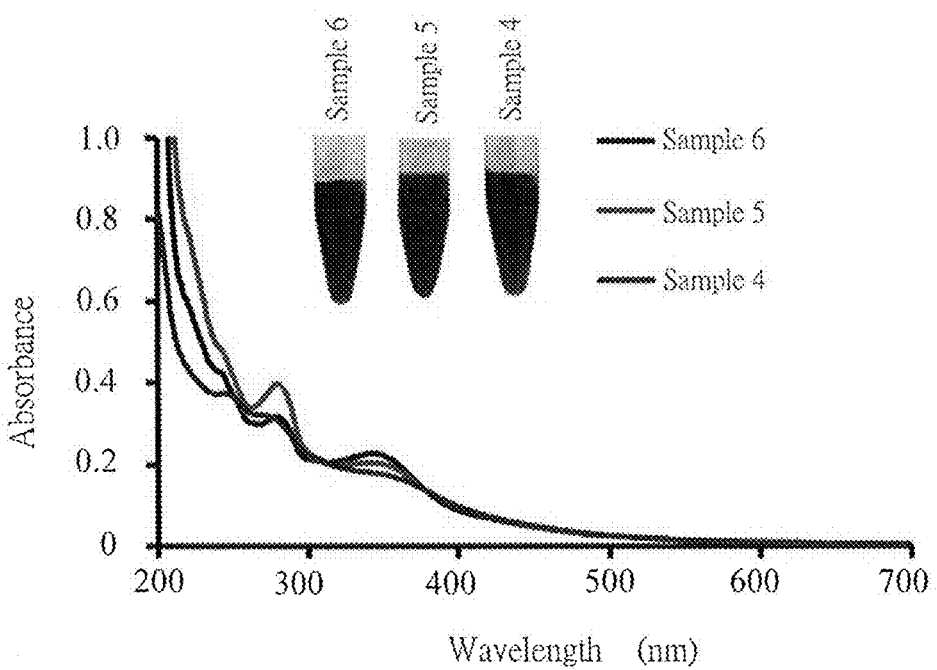
FIG. 4 shows the UV-visible absorption spectra of samples 4-6 of Example 1, infra.
Figure 5:
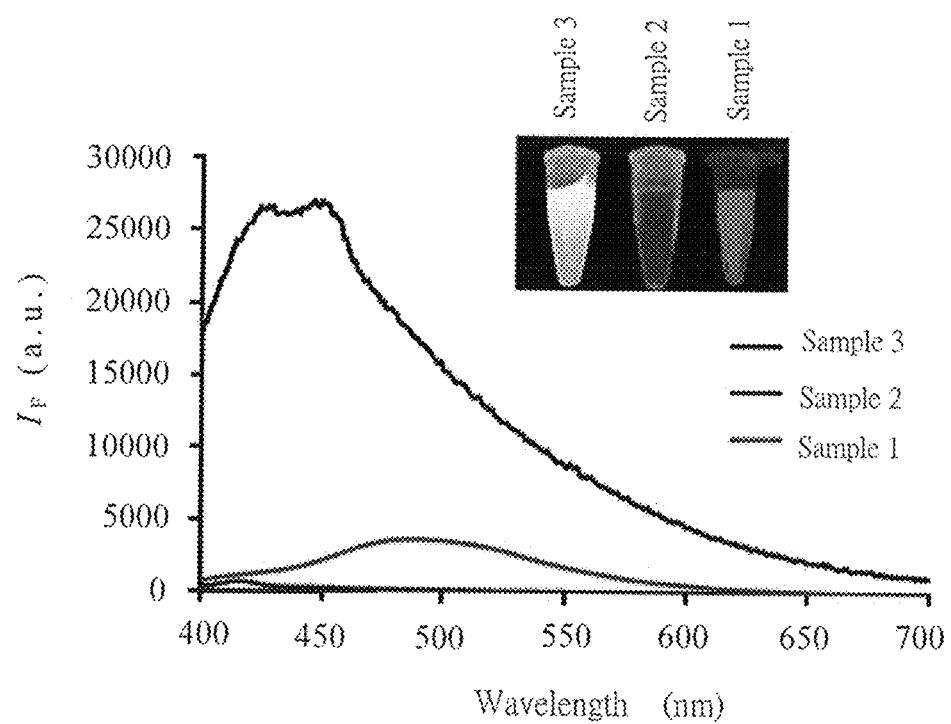
FIG. 5 shows the fluorescence spectra of samples 1-3 of Example 1, infra.
Figure 6:
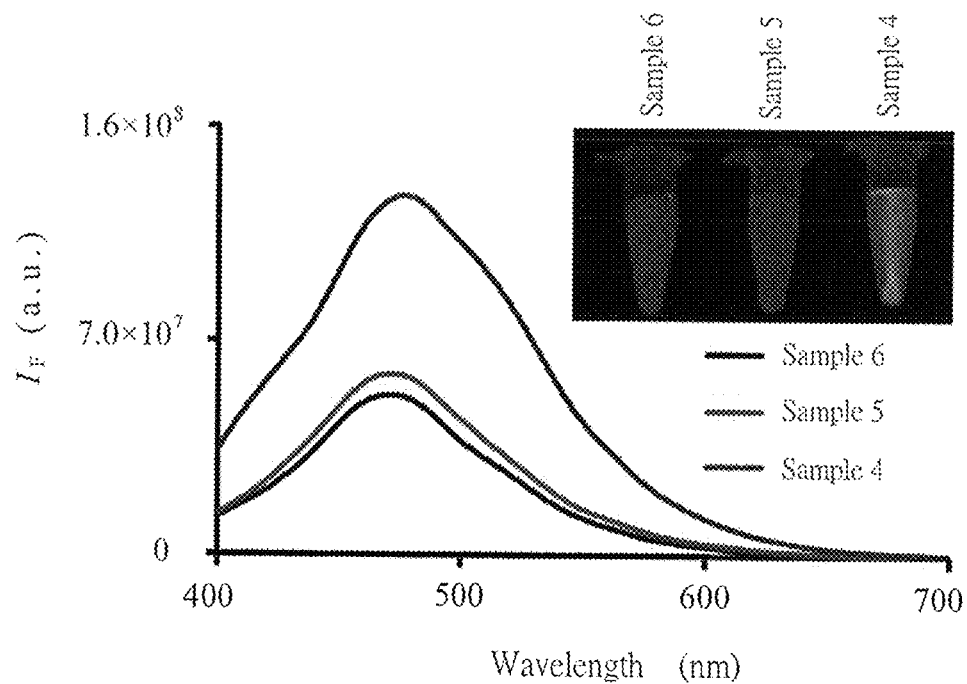
FIG. 6 shows the fluorescence spectra of samples 4-6 of Example 1, infra.

FIGS. 1-2 respectively show the UV-visible absorption spectra and the fluorescence spectra of the dialysates prepared at different pyrolysis temperatures. As shown in FIG. 1, when the pyrolysis of dopamine was carried out at a temperature of 230° C. or 250° C., a large amount of a deep black water-soluble pyrolysate was formed. In contrast, when the pyrolysis of dopamine was carried out at 270° C., only a few water-soluble pyrolysate was formed. In particular, the dialysate obtained at a pyrolysis temperature of 230° C. or 250° C. had a maximum absorbance at a wavelength in a range of from 275 nm to 300 nm, indicating that a π→π* conversion and a n→π* conversion occurred, resulting in the formation of C=O bonds and C=N bonds.

Moreover, only the dialysate obtained at a pyrolysis temperature of 250° C. had a fluorescent light emission intensity measured at a wavelength of 460 nm (see FIG. 2). The applicants then used 250° C. as the pyrolysis temperature in the subsequent experiments.

B. Pyrolysis of Dopamine with Various Polyamines at 250° C.

Samples 1-6 were prepared using the recipe shown in Table 2 and according to the method described in section A of this example, except that only the pyrolysis temperature of 250° C. was applied.

TABLE 2

| Samples | DA (g) | SPM (g) | SPD (g) | PUT (g) |
|---|---|---|---|---|
| Sample 1 | 0.04 | — | — | — |
| Sample 2 | — | 0.04 | — | — |
| Sample 3 | — | — | 0.04 | — |
| Sample 4 | 0.02 | 0.02 | — | — |
| Sample 5 | 0.02 | — | 0.02 | — |
| Sample 6 | 0.02 | — | — | 0.02 |

Subsequently, the resultant dialysate of each sample was collected and then subjected to UV-visible absorption spectroscopy and fluorescence spectroscopy as described in section A of this example.

Referring to FIGS. 3-6, the dialysate of each of samples 1 and 3-6 had a large amount of deep black water-soluble pyrolysate, and had a maximum absorbance at a wavelength in a range of from 275 nm to 300 nm and a fluorescent light emission intensity measured at a wavelength of 460 nm. In contrast, the dialysate of sample 2 had a few water-soluble pyrolysate, and no UV-visible absorbance spectrum and fluorescent light emission intensity were observed for the dialysate of sample 2.

This result indicated that pyrolysis of spermidine or pyrolysis of dopamine with various polyamines (e.g., spermine, spermidine, and putrescine) at 250° C. can successfully generate carbon quantum dots. The carbon quantum dots of samples 1 and 3-6 are represented by $CQD^{DA}$, $CQD^{SPD}/CQD^{DA-SPM}$, $CQD^{DA-SPD}$, and $CQD^{DA-PUT}$, respectively.

C. Morphological Analysis

Morphological analysis of $CQD^{DA-SPM}$ obtained in section B of this example was performed using a Tecnai G2 S-Twin transmission electron microscope (Philips/FEI, Hillsboro, Oreg., USA). The experimental results show that $CQD^{DA-SPM}$ had a particle size of about 4 nm and a lattice fringe of about 0.23 nm.

D. Fourier Transform Infrared Spectroscopy (FTIR)

A suitable amount of a respective one of $CQD^{DA}$, $CQD^{SPD}$, and $CQD^{DA-SPM}$ obtained in section B of this example and spermidine was freeze-dried, and the respective resultant freeze-dried powder was mixed with potassium bromide in a ratio of 1:99 (wt/wt), followed by compressing into a tablet. Each tablet was subjected to FTIR analysis using an Agilent Cary 640 FT-IR spectrometer (Santa Clara, Calif., USA).

Figure 7:
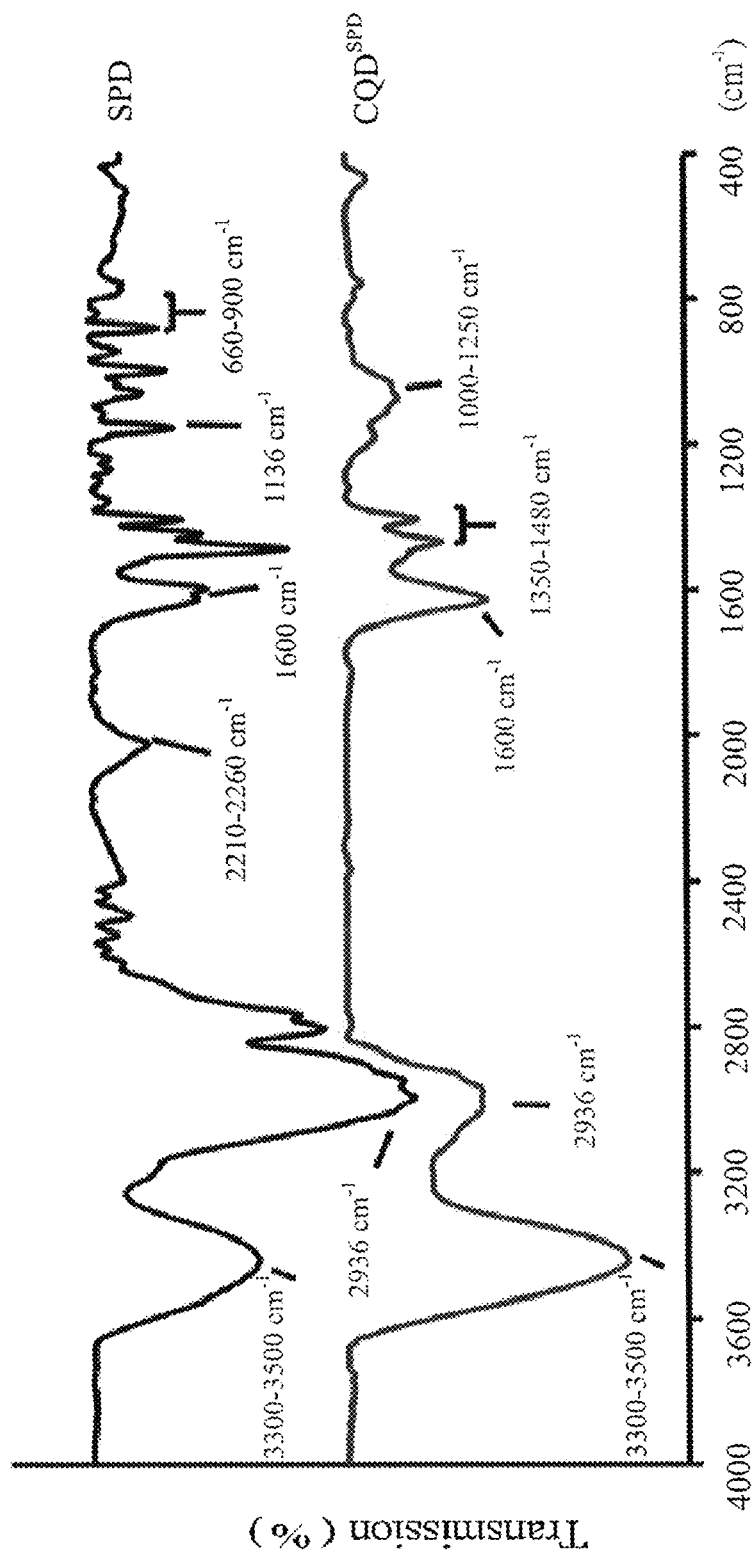
FIG. 7 shows the fourier transform infrared spectroscopy (FTIR) spectra of $CQD^{SPD}$ and spermidine (SPD)
Figure 8:
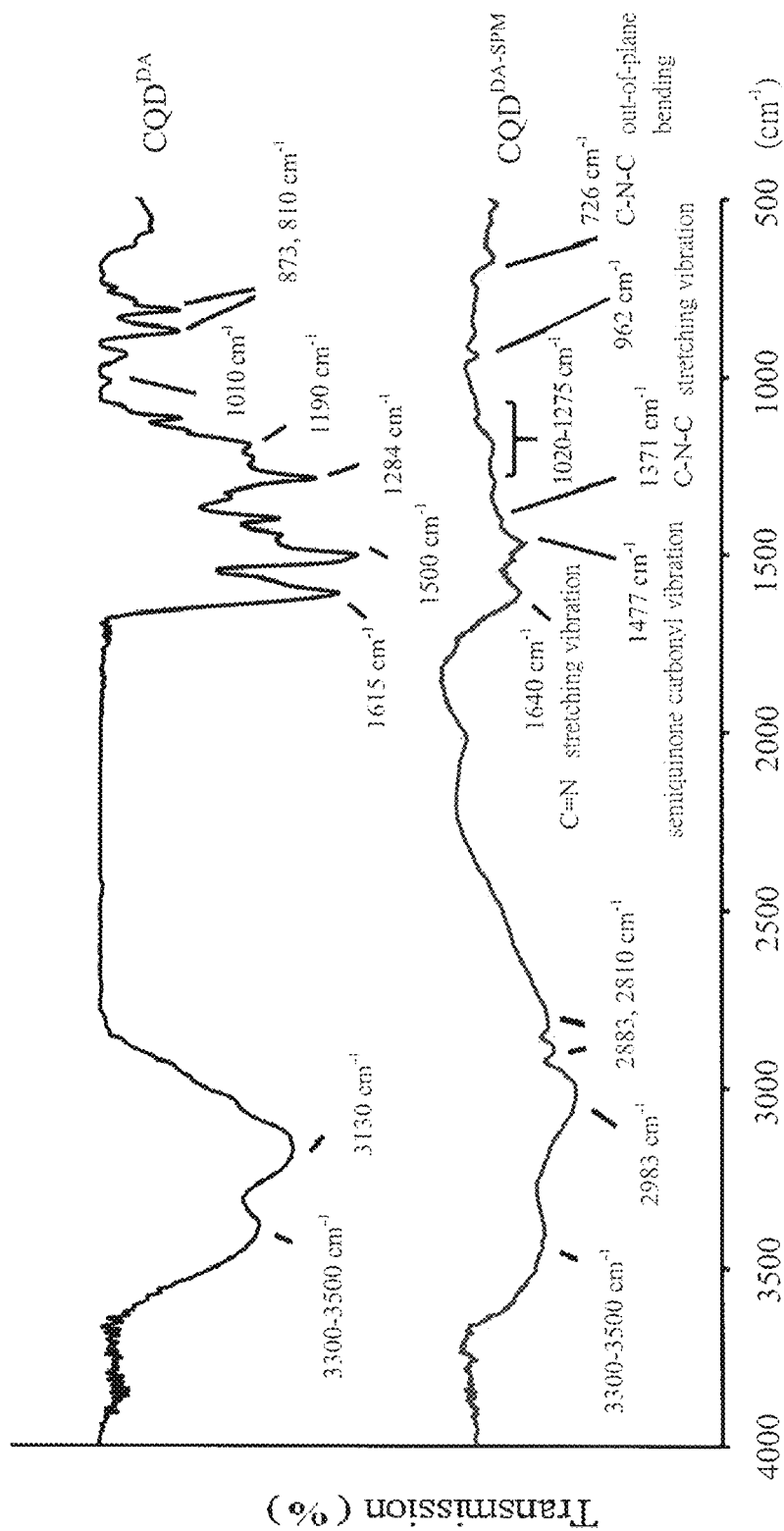
FIG. 8 shows the FTIR spectra of $CQD^{DA\text{-}SPM}$ and $CQD^{DA}$.

Referring to FIGS. 7-8, the FTIR spectrum of $CQD^{DA-SPM}$ different from those of $CQD^{DA-SPM}$, $CQD^{SPD}$, and spermidine. In particular, $CQD^{DA-SPM}$ had several absorption bands at 726 cm$^{-1}$ (C—N—C out-of-plane bending), 1371 cm$^{-1}$ (C—N—C stretching vibration), 1477 cm$^{-1}$ (semiquinone carbonyl vibration), and 1640 cm$^{-1}$ (C=N stretching vibration). These results indicate that the bonding and structural properties of $CQD^{DA-SPM}$ are different from those of $CQD^{DA}$, $CQD^{SPD}$, and spermidine.

E. X-Ray Photoelectron Spectroscopy (XPS)

The atomic ratio (N/C) of nitrogen and carbon at an outermost surface of $CQD^{SPD}$ and $CQD^{DA-SPM}$ obtained in section B of this example was measured using an ESCALAB 250 spectrometer (VG Scientific, East Grinstead, UK). The operating conditions applied are described as follows. The X-ray excitation source was Al Kα X-ray, and peaks of C1s and N1s were measured.

Figure 9:
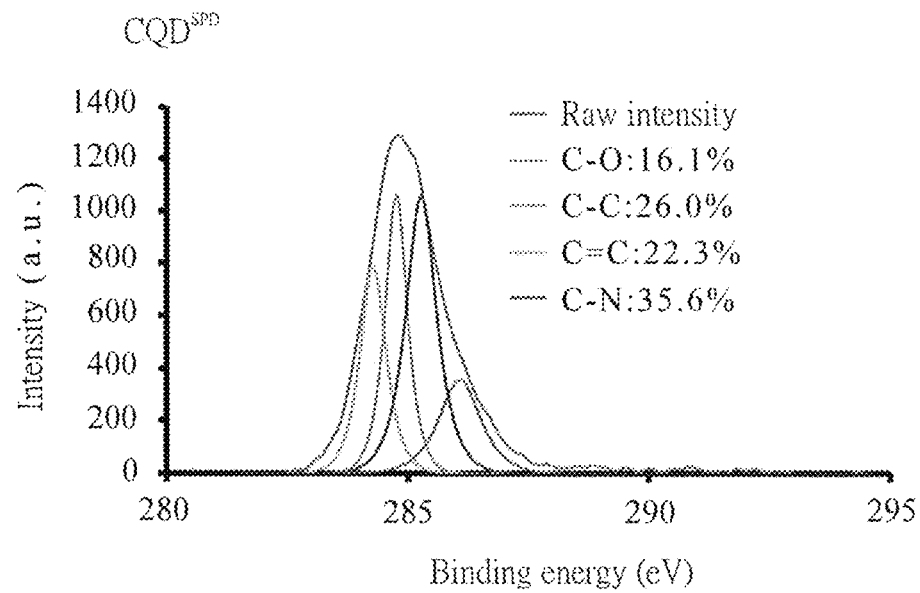
FIG. 9 shows the C1s peaks in the x-ray photoelectron spectroscopy (XPS) spectrum of $CQD^{SPD}$.
Figure 10:
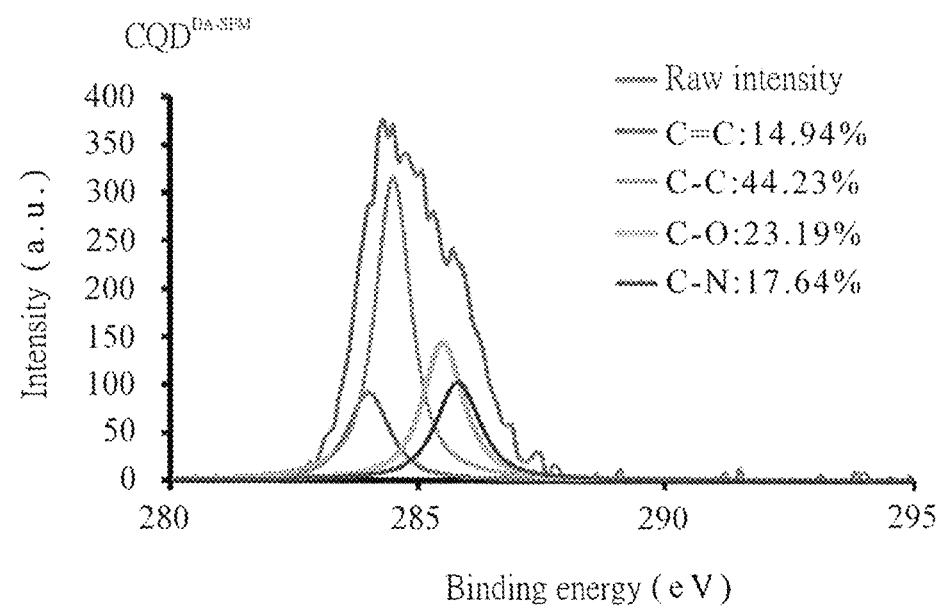
FIG. 10 shows the C1s peaks in the XPS spectrum of $CQD^{DA-SPM}$.

Referring to FIGS. 9-10, the relative proportions of various carbon bonds formed on the surface of $CQD^{SPD}$ are significantly different from those of $CQD^{DA-SPM}$.

Figure 11:
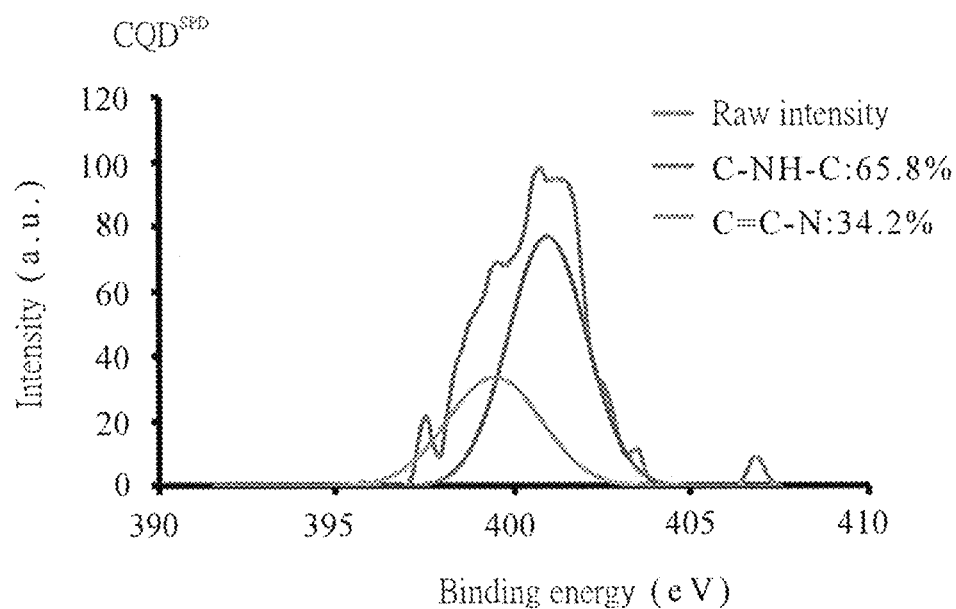
FIG. 11 shows the N1s peaks in the XPS spectrum of $CQD^{SPD}$.
Figure 12:
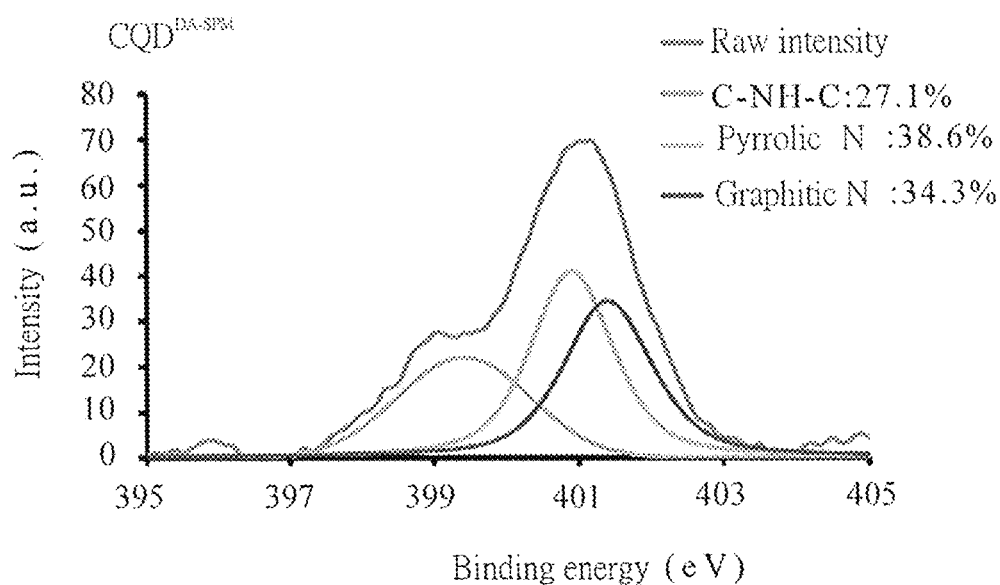
FIG. 12 shows the N1s peaks in the XPS spectrum of $CQD^{DA-SPM}$.

Referring to FIGS. 11-12, the relative proportions of various nitrogen bonds formed on the surface of $CQD^{SPD}$ are significantly different from those of $CQD^{DA-SPM}$.

These results indicate that the chemical bonding and bonding structure on the surface of $CQD^{DA-SPM}$ are different from those of $CQD^{SPD}$.

F. Zeta Potential Analysis

A suitable amount of a respective one of $CQD^{DA}$, $CQD^{DA-SPM}$, $CQD^{DA-SPD}$, and $CQD^{DA-PUT}$ obtained in section B of this example was dissolved in a 5 mM phosphate buffer (pH 7.4). The respective resultant mixture was subjected to zeta potential analysis using a Zetasizer Nano instrument (Nano ZS, Malvern Instruments, Worcestershire, UK).

Figure 13:
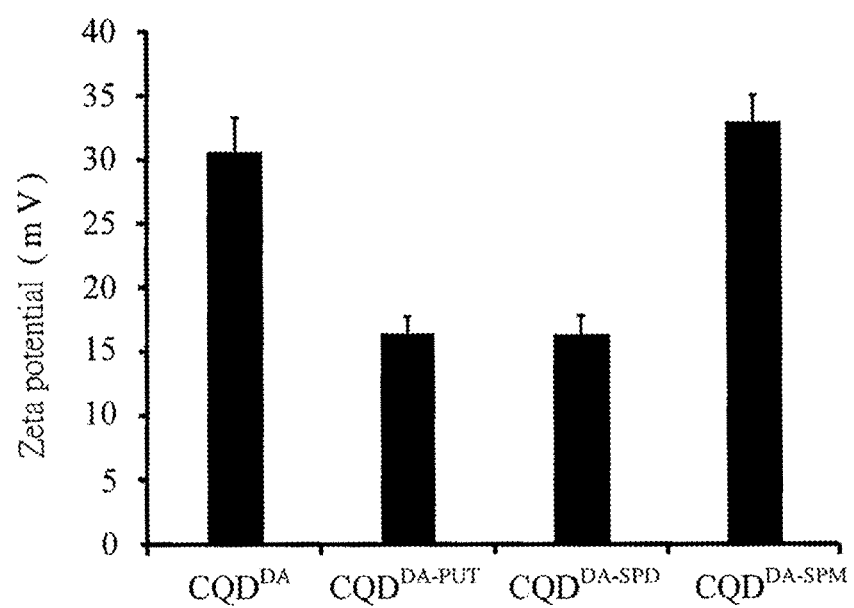
FIG. 13 shows the zeta potentials of $CQD^{DA}$, $CQD^{DA-SPM}$, $CQD^{DA-SPD}$, and $CQD^{DA-PUT}$.

Referring to FIG. 13, the zeta potential of each of $CQD^{DA}$ and $CQD^{DA-SPM}$ was significantly higher than those of $CQD^{DA-SPD}$ and $CQD^{DA-PUT}$. In particular, $CQD^{DA-SPM}$ had the highest zeta potential. These results indicate that $CQD^{DA-SPM}$ has a high positive surface charge.

Example 2. Antimicrobial Test

A. Preparation of Tested Bacterial Strains

A respective one of *Staphylococcus aureus, Escherichia coli, Pseudomonas aeruginosa, Salmonella enteritidis*, and MRSA was inoculated into a LB broth, followed by incubation in a thermostatic shaking incubator (37° C.) until an $OD_{600}$ value of 1.0 was reached. The respective resultant culture was centrifuged at 3,000 g for 10 minutes, and the cell pellet thus obtained was washed with a 5 mM phosphate buffer (pH 7.4), followed by suspending with a LB broth. The resultant bacterial broths of *Staphylococcus aureus, Escherichia coli, Pseudomonas aeruginosa, Salmonella enteritidis*, and MRSA (each of such five bacterial suspensions contained a bacterial concentration of 1×10$^4$ CFU/mL) were used for the following experiment.

B. Preparation of $CQD^{DA-SPM-1}$ and $CQD^{DA-SPM-2}$ $CQD^{DA-SPM-1}$ and $CQD^{DA-SPM-2}$ were prepared generally according to the procedures described in the abovementioned section B of Example 1, except that: for $CQD^{DA-SPM-1}$, the ratio of dopamine to spermine is 1:2.33 (w/w), and for $CQD^{DA-SPM-2}$, the ratio of dopamine to spermine is 1:0.42 (w/w).

C. Preparation of DA Solutions and SPM Solutions

A suitable amount of a respective one of dopamine and spermine was dissolved in deionized water, so as to obtain DA solutions having different concentrations (0.05-5000 μg/mL), and SPM solutions having different concentrations (0.05-5000 μg/mL).

D. Preparation of CQD Solutions

A suitable amount of a respective one of $CQD^{DA}$, $CQD^{SPD}$, $CQD^{DA\text{-}SPM}$, $CQD^{DA\text{-}SPD}$, $CQD^{DA\text{-}PUT}$, $CQD^{DA\text{-}SPM\text{-}1}$, and $CQD^{DA\text{-}SPM\text{-}2}$ was freeze-dried, and the respective resultant freeze-dried powder was dissolved in deionized water, followed by dilution with a 5 mM phosphate buffer (pH 7.4), so as to obtain seven CQD solutions having different concentrations (0.05-50 μg/mL).

E. Evaluation of Antimicrobial Effect of $CQD^{DA\text{-}SPM}$

A respective one of the five CQD solutions (i.e., $CQD^{DA}$, $CQD^{SPD}$, $CQD^{DA\text{-}SPM}$, $CQD^{DA\text{-}SPD}$, and $CQD^{DA\text{-}PUT}$ solutions), the DA solutions, and the SPM solutions and a respective one of the bacterial broths of *Staphylococcus aureus* and *Escherichia coli* were mixed in a 5 mM phosphate buffer (pH 7.4), and the respective resultant mixture was incubated in a thermostatic shaking incubator (37° C.) for 1 hour, followed by addition of a suitable amount of LB broth. After incubation with shaking for 18 hours, the respective resultant culture was subjected to serial dilution with a LB broth, so as to obtain seven dilutions ($10^1$ to $10^7$).

Thereafter, 1 μL of the respective dilution was subjected to spread plate procedure. The number of surviving bacteria was counted, and the minimum inhibitory concentration to inhibit the growth of 90% of a bacterial isolate ($MIC_{90}$) was determined according to the technique well known to and routinely used by one skilled in the art.

As shown in Table 3 below, for *Staphylococcus aureus* and *Escherichia coli*, the $MIC_{90}$ values of $CQD^{DA\text{-}SPM}$ were significantly lower than those of the other four CQDs, DA, and SPM, indicating that the $CQD^{DA\text{-}SPM}$ of the present disclosure is effective in inhibiting the growth of bacteria.

TABLE 3

|  | Staphylococcus aureus | Escherichia coli |
|---|---|---|
|  | $MIC_{90}$ (μg/mL) | |
| $CQD^{DA}$ | 30.0 | 34.2 |
| $CQD^{SPD}$ | 23.1 | 35.2 |
| $CQD^{DA\text{-}SPM}$ | 4.8 | 3.9 |
| $CQD^{DA\text{-}SPD}$ | >50 | >50 |
| $CQD^{DA\text{-}PUT}$ | >50 | >50 |
| DA | 250 | 512 |
| SPM | 658.3 | 2350.4 |

F. Evaluation of Antimicrobial Effect of $CQD^{DA\text{-}SPM}$, $CQD^{DA\text{-}SPM\text{-}1}$, and $CQD^{DA\text{-}SPM\text{-}2}$ A respective one of the four CQD solutions (i.e., $CQD^{DA}$, $CQD^{DA\text{-}SPM}$, $CQD^{DA\text{-}SPM\text{-}1}$, and $CQD^{DA\text{-}SPM\text{-}2}$ solutions) and the SPM solutions and a respective one of bacterial broths of *Staphylococcus aureus*, *Escherichia coli*, *Pseudomonas aeruginosa*, *Salmonella enteritidis*, and MRSA were mixed in a 5 mM phosphate buffer (pH 7.4), and the respective resultant mixture was subjected to antimicrobial activity analysis according to the method described in section E of this example.

As shown in Table 4 below, for the five bacterial pathogens, the $MIC_{90}$ values of $CQD^{DA\text{-}SPM}$, $CQD^{DA\text{-}SPM\text{-}1}$, and $CQD^{DA\text{-}SPM\text{-}2}$ were significantly lower than those of $CQD^{DA}$ and SPM, indicating that the $CQD^{DA\text{-}SPM}$, $CQD^{DA\text{-}SPM\text{-}1}$, and $CQD^{DA\text{-}SPM\text{-}2}$ of the present disclosure are effective in inhibiting the growth of bacteria.

TABLE 4

|  | Staphylococcus aureus | Escherichia coli | Pseudomonas aeruginosa | Salmonella enteritidis | MRSA |
|---|---|---|---|---|---|
|  |  |  | $MIC_{90}$ (μg/mL) |  |  |
| $CQD^{DA}$ | 30.0 | 34.2 | 70.6 | 31.8 | 33.2 |
| $CQD^{DA\text{-}SPM}$ | 6.3 | 7.5 | 6.3 | 6.5 | 7.08 |
| $CQD^{DA\text{-}SPM\text{-}1}$ | 4.8 | 3.9 | 4.4 | 4.3 | 4.72 |
| $CQD^{DA\text{-}SPM\text{-}2}$ | 4.9 | 4.6 | 4.3 | 3.7 | 3.8 |
| SPM | 658.3 | 2350.4 | 2453.4 | 2655.7 | 1552.5 |

Example 3. Antimicrobial Effect of $CQD^{DA\text{-}SPM}$ on Contact Lens

Materials:

A. Preparation of $CQD^{DA\text{-}SPM}$ Solutions

A suitable amount of $CQD^{DA\text{-}SPM}$ was dissolved in deionized water, so as to obtain two $CQD^{DA\text{-}SPM}$ solutions respectively having 100 and 200 μg/mL of $CQD^{DA\text{-}SPM}$.

Methods:

Contact lenses (Alcon, DAILIES DAILIES® AquaComfort Plus®) were divided into 3 groups, including two experimental groups (i.e., experimental groups 1 and 2) and one control group (n=2 for each group). The contact lenses of the experimental group 1 and the experimental group 2 were respectively immersed in 100 μg/mL $CQD^{DA\text{-}SPM}$ solution and 200 μg/mL $CQD^{DA\text{-}SPM}$ solution, and the contact lenses of the control group were not treated with $CQD^{DA\text{-}SPM}$. The contact lenses of each group were respectively added to the bacterial broth of *Staphylococcus aureus* prepared in section A of Example 2 (the concentration of the bacterial broth was adjusted to $1 \times 10^8$ CFU/mL). All the groups were cultivated in an incubator (37° C.) for 48 hours.

Thereafter, the contact lenses of each group were taken out, and biofilm formation was visually observed. Subsequently, 2 mL of phosphate-buffered saline (PBS) was added to a respective one of the contact lenses of each group, followed by shaking for 9 minutes. Subsequently, the resultant liquid portion was collected and was diluted 10-fold by PBS. 100 μL of the respective resultant dilution was obtained, and was coated onto a LB agar plate using spread plate technique, followed by cultivation in an incubator (37° C.) for 18 hours. The number of colonies on the LB agar plates of each group was counted, and the total bacterial count of each group was further calculated based on the dilution ratio. The bacterial viability percentage (%) was calculated using the following Equation (I):

$$A = (B/C) \times 100 \qquad (I)$$

where A=the bacterial viability percentage (%)

B=the total bacterial count of experimental group 1 or 2

C=the total bacterial count of the control group

Figure 14:
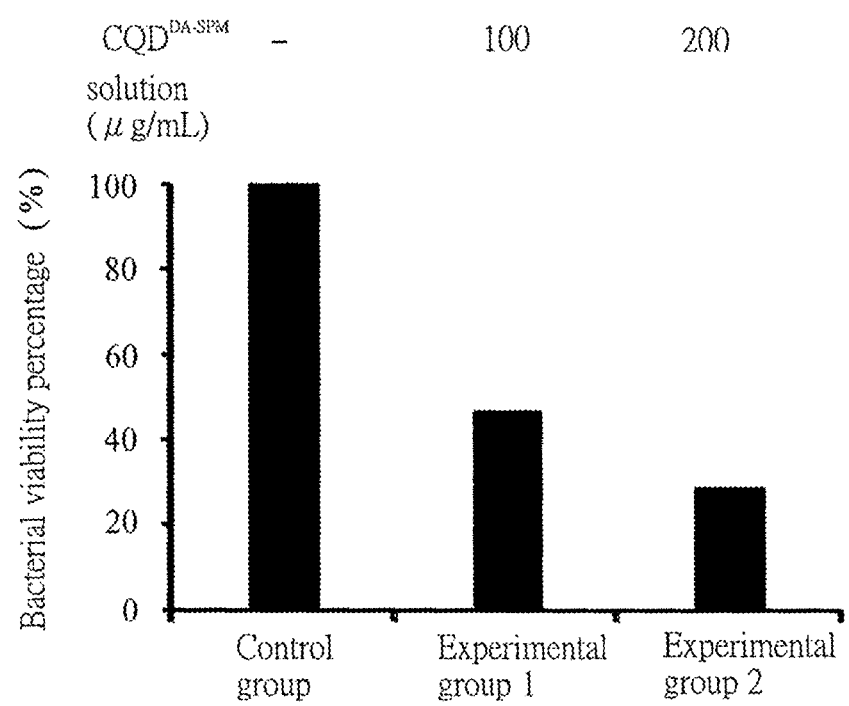
FIG. 14 shows the bacterial viability percentage of each group of Example 3, infra.

Results:

Referring to FIG. 14, the bacterial viability percentages of the experimental groups 1 and 2 were significantly lower than that of the control group. Moreover, a significant dose-dependent effect of the $CQD^{DA\text{-}SPM}$ of the present disclosure on the bacterial viability percentage was observed. In addition, biofilm formation was not observed in the experimental groups 1 and 2, while in the control group, biofilm formation was observed.

This result indicates that the CQD$^{DA\text{-}SPM}$ of the present disclosure is effective in inhibiting growth of biofilm associated bacteria and killing biofilm associated bacteria, and hence can be used as an anti-biofilm agent for inhibiting bacterial growth and biofilm formation on an object (such as a medical device, a bandage, a food preparation surface, a consumer good, a water delivery system, etc.).

Example 4. Evaluation for the Effect of CQD$^{DA\text{-}SPM}$ on Treating Bacterial Keratitis A. Test Animals New Zealand white rabbits (16-20 weeks old, a body weight of 3-3.5 Kg) were purchased from National Laboratory Animal Breeding and Research Center (Taipei, Taiwan, ROC). The rabbits were kept in an animal room with an independent air conditioning system under the following laboratory conditions: a 12 hour light/12 hour dark cycle, a temperature of 20-24° C., and a relative humidity of 55-65%. Furthermore, water and feed were provided ad libitum for all the experimental animals. All animal testing procedures were approved by the National Institutes of Health and were carried out in accordance with the ARVO Statement for the Use of Animals in Ophthalmic and Vision Research.

B. Preparation of CQD$^{DA\text{-}SPM}$-Treated Contact Lenses

Contact lenses (Alcon, DAILIES DAILIES® AquaComfort Plus®) were immersed in 200 μg/mL CQD$^{DA\text{-}SPM}$ solution prepared in section A of Example 3 for 1 hour, and the thus obtained CQD$^{DA\text{-}SPM}$-treated contact lenses were used for the following experiment.

C. Induction of Bacterial Keratitis

The New Zealand white rabbits were divided into a control group and an experimental group (n=6 for each group). The cornea of each rabbit in the experimental group and the control group was cut to form a wound having an area of about 3 mm×3 mm using sterile surgical scissors and a blade. Thereafter, 50 μL of the bacterial broth of Staphylococcus aureus prepared in section A of Example 2 (the concentration of the bacterial broth was adjusted to 1×10$^8$ CFU/mL) was topically instilled into the ocular surface of the respective rabbit, so as to induce bacterial keratitis.

D. Application of CQD$^{DA\text{-}SPM}$-Treated Contact Lenses

The upper and lower eyelids of each rabbit were passively kept closed for 2 minutes, and thereafter, for the experimental group, the CQD$^{DA\text{-}SPM}$-treated contact lens obtained in the above section B was placed on the eye of each rabbit. For the control group, an untreated contact lens was placed on the eye of each rabbit. After a 4-hour rest, the contact lens was removed from the eye of each rabbit. On Day 0.5, Day 1, and Day 3 after the treatment, the eye of each rabbit was subjected to analyses set forth in sections E and F below. Furthermore, Day 14 after the treatment, all the rabbits were sacrificed by virtue of 95% $CO_2$, and the corneal tissue of the respective rabbit was obtained using a sterile surgical blade, and was subjected to analyses set forth in sections E and F below.

E. Morphological Observation

The change in anterior segment morphometry of each rabbit was analyzed using a method slightly modified from that described by Jian H. J. et al. (2017), *ACS Nano*, 11:6703-6716. Briefly, the anterior segment morphology (i.e., corneal and lens clarity, the degree of anterior chamber activity, and status of iris) of the rabbit eye was observed by slit-lamp biomicroscopy (Topcon Optical, Tokyo, Japan), and seven parameters, including conjuncitivitis, chemosis, iritis, fibrin accumulation, hypopyon, stromal infiltration, and stromal edema, were assessed visually by scoring on a scale from 0 to 4 (the higher the scale, the more serious the ocular symptom was).

Figure 15:
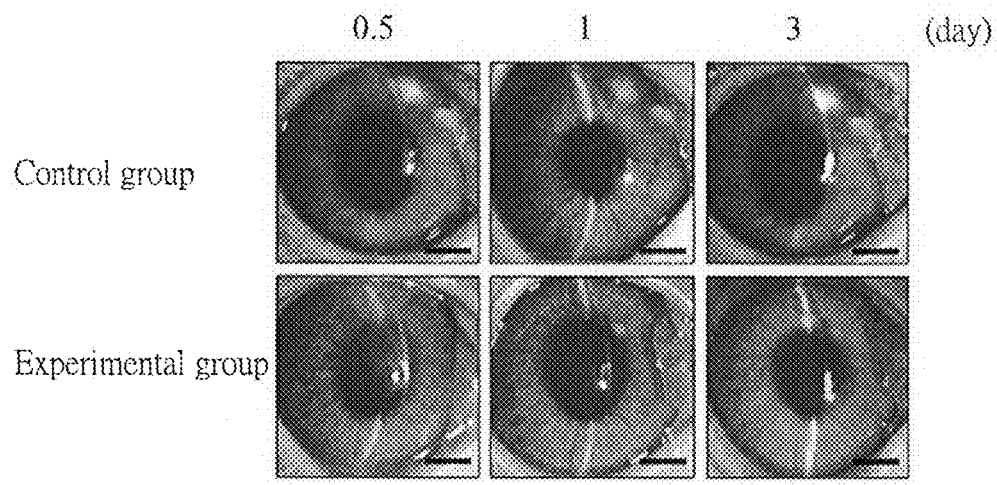
FIG. 15 shows the slit-lamp biomicroscopic images of rabbit eyes on Day 0.5, Day 1, and Day 3 after treatment.
Figure 16:
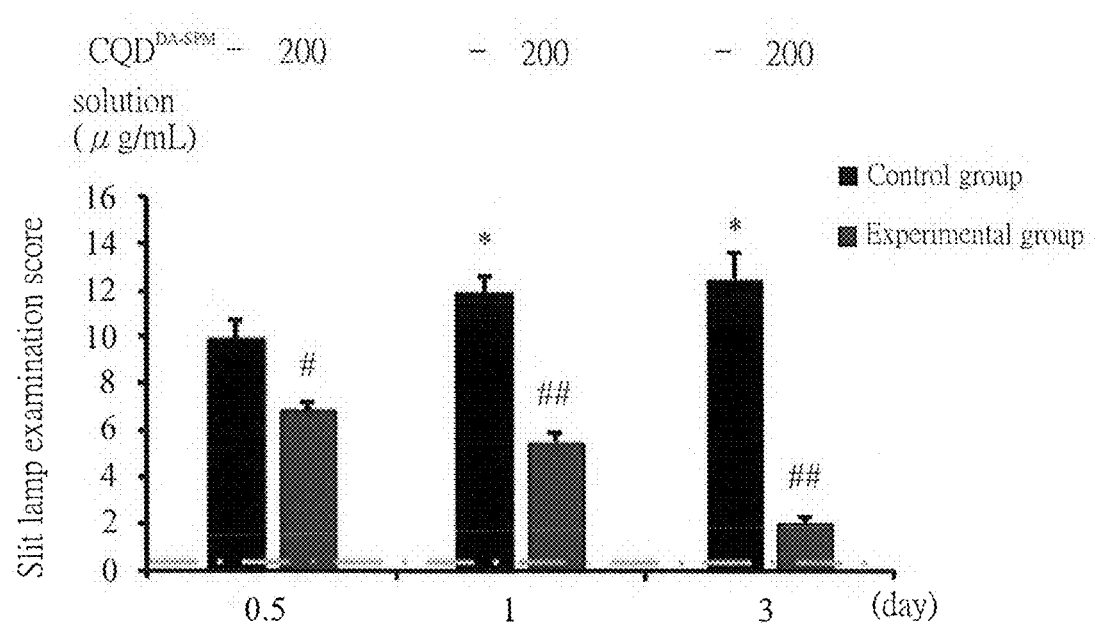
FIG. 16 shows the the slit lamp examination scores of the rabbit eyes on Day 0.5, Day 1, and Day 3 after treatment, in which the symbol "*" represents $p<0.05$ (compared with the control group on Day 0.5), the symbol "#" represents $p<0.05$ (compared with the control group on Day 0.5), and the symbol "##" represents $p<0.01$ (compared with the control group on a corresponding one of Day 1 and Day 3)

Referring to FIGS. 15-16, in the control group, the development of empyema, infiltration, and edema was significantly observed with time, and the slit lamp examination score was increased with time. In contrast, in the experimental group, the empyema, infiltration, and edema were significantly ameliorated with time, and the slit lamp examination score was significantly decreased with time.

F. Determination of Central Corneal Thickness

The central corneal thickness of each rabbit was determined using an ultrasonic pachymeter equipped with a hand-held solid probe (DGH Technology, Exton, Pa., USA).

Figure 17:
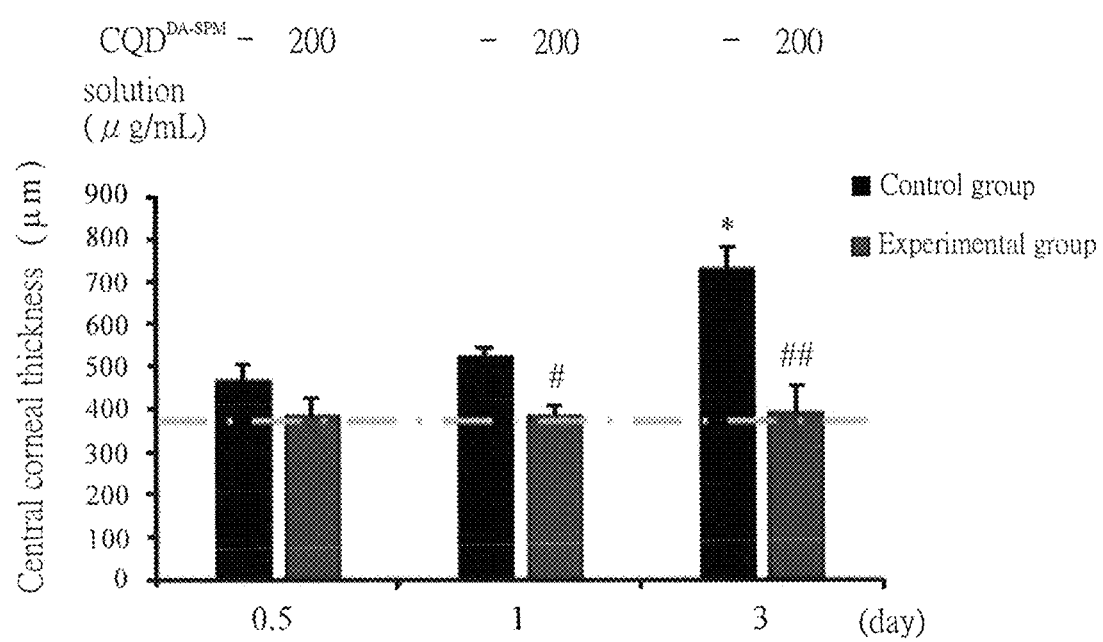
FIG. 17 shows the central corneal thickness of each group of Example 4, infra, in which the symbol "*" represents $p<0.05$ (compared with the control group on Day 0.5), the symbol "#" represents $p<0.05$ (compared with the control group on Day 1), and the symbol "##" represents $p<0.01$ (compared with the control group on Day 3)

Referring to FIG. 17, on Day 1 and Day 3 after the treatment, the central corneal thickness of the experimental group was significantly lower than that of the control group.

G. Histopathologic Analysis 0.02 g of the corneal tissue of each group was fixed with a 4% paraformaldehyde solution (in PBS) at room temperature for 2 hours, and the fixed tissue sample was then embedded with paraffin, followed by slicing to obtain a tissue section having a thickness of 5 μm. The tissue section was stained using a hematoxylin and eosin (H&E) staining protocol well-known to those skilled in the art, and was observed under an optical microscope (Carl Zeiss, Oberkochen, Germany) at 200× magnification.

Figure 18:
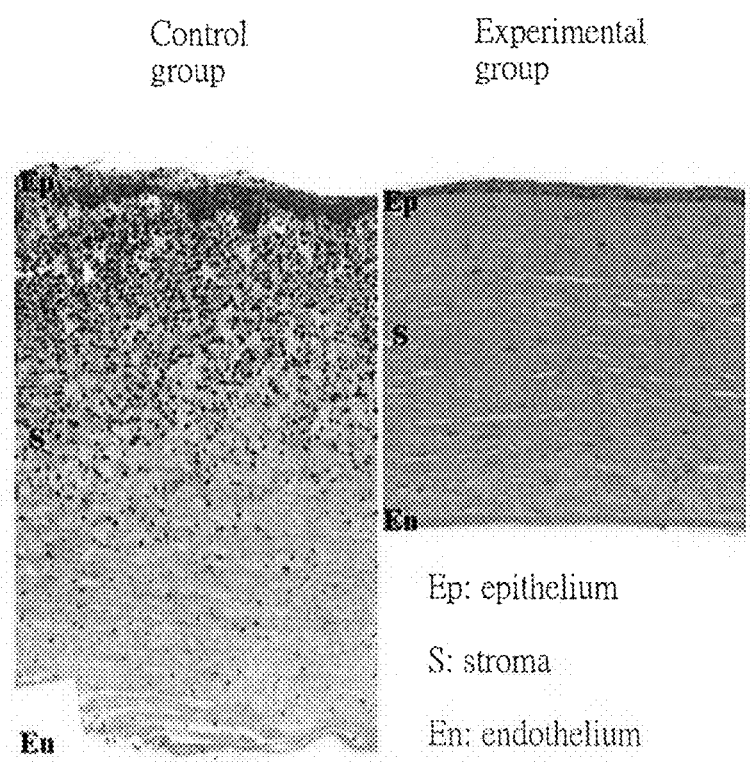
FIG. 18 shows the histological observation result of each group of Example 4, infra.

Referring to FIG. 18, in the control group, the corneal tissue has an abnormal structure, and severe infiltration of inflammatory cells was observed in the stroma. In contrast, in the experimental group, the corneal tissue had a normal structure and no infiltration was observed.

H. Determination of Viable Bacteria Count 0.2 g of the corneal tissue of the respective group was added to 2 mL of PBS, and the thus obtained mixture was homogenized using a homogenizer, and was then diluted 20-fold by PBS. 0.1 mL of the respective dilution was coated onto a mannitol salt agar (MSA) plate (containing 10 g/L mannitol, 75 g/L NaCl, 10 g/L peptone, 1 g/L beef extract, and 15 g/L agar) using spread plate technique, followed by cultivation in an incubator (37° C.) for 24 hours. The number of colonies on the MSA plate of each group was counted, and the total bacterial count of each group was further calculated based on the dilution ratio.

Figure 19:
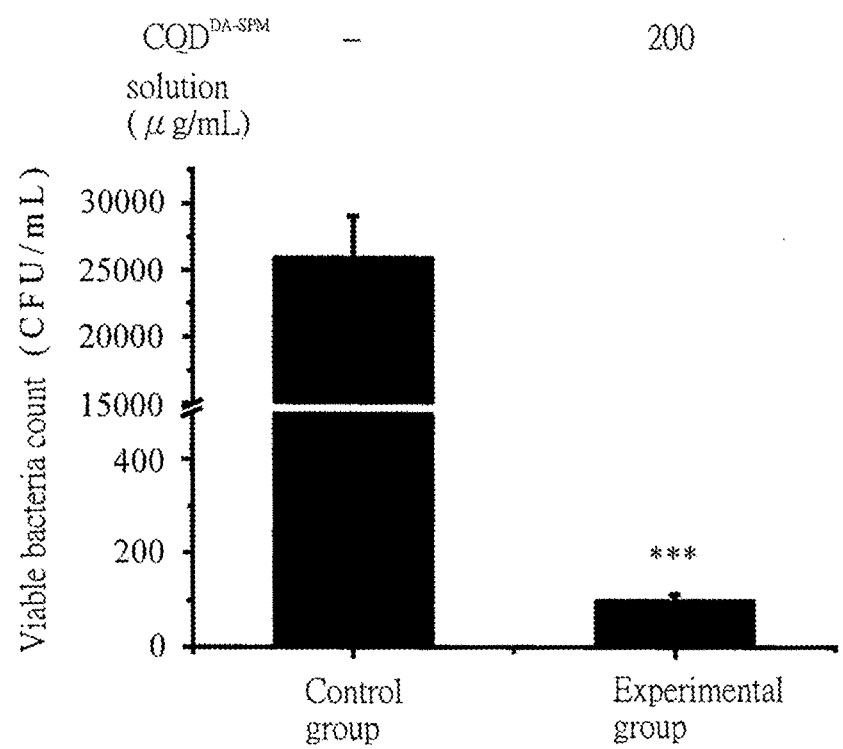
FIG. 19 shows the viable bacteria count of each group of Example 4, infra, in which the symbol "* * *" represents $p<0.005$ (compared with the control group).

Referring to FIG. 19, the viable bacteria count of the experimental group was significantly lower than that of the control group.

Summarizing the above test results, it is clear that the CQD$^{DA\text{-}SPM}$ of the present disclosure is effective in treating a bacterial infection and inhibiting bacterial growth and biofilm formation.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A carbon quantum dot produced by the step of: subjecting a mixture of dopamine and spermine to a pyrolysis treatment at 250° C.

2. The carbon quantum dot according to claim 1, wherein a ratio of dopamine to spermine ranges from 1:0.25 (w/w) to 1:4 (w/w).

3. The carbon quantum dot according to claim 1, which has a particle size ranging from 3 to 10 nm.

4. The carbon quantum dot according to claim 1, which has a zeta potential ranging from +5 to +50 mV.

5. A composition comprising one or more of a carbon quantum dot as claimed in claim 1.

6. A method for treating a bacterial infection, comprising administering to a subject in need thereof one or more of a carbon quantum dot as claimed in claim 1.

7. A method for inhibiting bacterial growth and biofilm formation, comprising applying one or more of a carbon quantum dot as claimed in claim 1 onto an object.

8. A process for producing a carbon quantum dot, comprising the step of: subjecting a mixture of dopamine and spermine to a pyrolysis treatment at 250° C.

9. The process according to claim 8, wherein a ratio of dopamine to spermine ranges from 1:0.25 (w/w) to 1:4 (w/w).

* * * * *